(12) United States Patent
Miller et al.

(10) Patent No.: US 7,476,771 B2
(45) Date of Patent: Jan. 13, 2009

(54) AZEOTROPE COMPOSITIONS COMPRISING 2,3,3,3-TETRAFLUOROPROPENE AND HYDROGEN FLUORIDE AND USES THEREOF

(75) Inventors: Ralph Newton Miller, Newark, DE (US); Mario Joseph Nappa, Newark, DE (US); Velliyur Nott Mallikarjuna Rao, Wilmington, DE (US); Allen Capron Sievert, Elkton, MD (US)

(73) Assignee: E.I. Du Pont De Nemours + Company, Wilmington, DE (US)

( * ) Notice: Subject to any disclaimer, the term of this patent is extended or adjusted under 35 U.S.C. 154(b) by 0 days.

(21) Appl. No.: 11/590,454

(22) Filed: Oct. 31, 2006

(65) Prior Publication Data

US 2007/0100175 A1    May 3, 2007

Related U.S. Application Data

(60) Provisional application No. 60/732,321, filed on Nov. 1, 2005.

(51) Int. Cl.
*C07C 17/38* (2006.01)
*C07C 17/00* (2006.01)

(52) U.S. Cl. .................. 570/178; 570/155

(58) Field of Classification Search .............. 570/155, 570/178

See application file for complete search history.

(56) References Cited

U.S. PATENT DOCUMENTS

| 4,766,260 | A |   | 8/1988  | Manzer et al.    |
|-----------|---|---|---------|------------------|
| 4,902,838 | A |   | 2/1990  | Manzer et al.    |
| 4,978,649 | A |   | 12/1990 | Surovikin et al. |
| 5,136,113 | A |   | 8/1992  | Rao              |
| 5,268,122 | A |   | 12/1993 | Rao et al.       |
| 5,396,000 | A |   | 3/1995  | Nappa et al.     |
| 5,918,481 | A | * | 7/1999  | Pham et al. ................... 62/631 |
| 6,369,284 | B1|   | 4/2002  | Nappa et al.     |
| 6,540,933 | B1|   | 4/2003  | Sievert et al.   |
| 2006/0094911 | A1 |   | 5/2006 | Rao et al.     |

FOREIGN PATENT DOCUMENTS

| JP |          0 328 148 A1 | 8/1989 |
| JP |     WO 2005/108334 A1 | 11/2005 |
| WO |     WO 2005/103191 A2 | 11/2005 |

OTHER PUBLICATIONS

Szapiro, variation of azeotropic composition with pressure, Zesyty Nauk. Politech. Lodz. Chem. (1958), No. 7, 3-16.*
Schotte, "Collection of Phase Equilibrium Data for Separation Technology", Ind. Eng. Chem. Process Des. Dev. 19 (1980), pp. 432-439.
Null, "Phase Equilibrium in Process Design", Wiley-Interscience Publisher (1970), pp. 124-126.
Walas, "Phase Equilibria in Chemical Engineering—Activity Coefficients", Butterworth Publishers (1985), pp. 165-244.
McDoniel et al., "Threshold Energy and Unimolecular Rate Constant for Elimination of HF from Chemically Activated CF3CF2CH3: Effect of the CF3 Substituent on the a-Carbon", J. Phys. Chem. A (1997), 101, pp. 1334-1337.
Orkin et al., "Rate Constants for the Reactions of OH with HFC-245cb (CH3CF2CF3) and Some Fluoroalkenes (CH2CHCF3, CH2CFCF3, CF2CFCF3, and CF2CF2)", J. Phys. Chem. A (1997), 101, pp. 9118-9124.
PCT International Search Report dated Jun. 6, 2007 for International Application No. PCT/US2006/042771.

* cited by examiner

*Primary Examiner*—Jafar Parsa
(74) *Attorney, Agent, or Firm*—Daniel Mark Maloney (57) ABSTRACT

Disclosed herein are azeotrope or near-azeotrope compositions comprising 2,3,3,3-tetrafluoropropene (HFC-1234yf) and hydrogen fluoride (HF). These compositions are useful in processes to produce and purify HFC-1234yf. Additionally, disclosed herein are processes for the manufacture of HFC-1234yf.

20 Claims, 1 Drawing Sheet

AZEOTROPE COMPOSITIONS COMPRISING 2,3,3,3-TETRAFLUOROPROPENE AND HYDROGEN FLUORIDE AND USES THEREOF

CROSS-REFERENCE TO RELATED APPLICATION

This application claims priority under 35 U.S.C. §119 from U.S. Provisional Application Ser. No. 60/732,321 (filed Nov. 1, 2005), which is incorporated by reference herein as if fully set forth.

BACKGROUND OF THE INVENTION

1. Field of the Invention

Disclosed herein are azeotrope compositions comprising 2,3,3,3-tetrafluoropropene and hydrogen fluoride. The azeotrope compositions are useful in processes to produce and in processes to purify 2,3,3,3-tetrafluoropropene.

2. Description of Related Art

Chlorine-containing compounds, such as chlorofluorocarbons (CFCs) are considered to be detrimental to the Earth's ozone layer. Many of the hydrofluorocarbons (HFCs), used to replace CFCs, have been found to contribute to global warming. Therefore, there is a need to identify new compounds that do not damage the environment, but also possess the properties necessary to function as refrigerants, solvents, cleaning agents, foam blowing agents, aerosol propellants, heat transfer media, dielectrics, fire extinguishing agents, sterilants and power cycle working fluids. Fluorinated olefins, containing one or more hydrogens in the molecule, are being considered for use in some of the applications, like for example in refrigeration.

BRIEF SUMMARY OF THE INVENTION

One aspect relates to an azeotrope or near-azeotrope composition comprising 2,3,3,3-tetrafluoropropene (HFC-1234yf, $CF_3CF=CH_2$) and hydrogen fluoride (HF).

A further aspect relates to a process for the separation of HFC-1234yf from 1,1,1,2,2-pentafluoropropane (HFC-245cb) comprising: a) forming a mixture of HFC-1234yf, HFC-245cb, and hydrogen fluoride; and b) subjecting said mixture to a distillation step from which is formed a column distillate composition comprising an azeotrope or near-azeotrope composition of hydrogen fluoride and HFC-1234yf essentially free of HFC-245cb.

A further aspect relates to a process for the separation of HFC-1234yf from a mixture comprising an azeotrope or near-azeotrope composition of HFC-1234yf and hydrogen fluoride, said process comprising: a) subjecting said mixture to a first distillation step in which a composition enriched in either (i) hydrogen fluoride or (ii) HFC-1234yf is removed as a first distillate composition with a first bottoms composition being enriched in the other of said components (i) or (ii); and b) subjecting said first distillate composition to a second distillation step conducted at a different pressure in which the component enriched as first bottoms composition in (a) is removed in a second distillate composition with a second bottoms composition enriched in the same component which was enriched in the first distillate composition.

A further aspect relates to a process for the purification of HFC-1234yf from a mixture of HFC-1234yf, HFC-245cb, and hydrogen fluoride, said process comprising: a) subjecting said mixture to a first distillation step to form a first distillate comprising an azeotrope or near-azeotrope composition containing HFC-1234yf and hydrogen fluoride and a first bottoms comprising HFC-245cb; b) subjecting said first distillate to a second distillation step from which a composition enriched in either (i) hydrogen fluoride or (ii) HFC-1234yf is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed as a third distillate composition with a third bottoms composition enriched in the same component that was enriched in the second distillate composition.

A further aspect relates to a process to produce HFC-1234yf comprising: a) feeding HFC-245cb to a reaction zone for dehydrofluorination to form a reaction product composition comprising HFC-1234yf, unreacted HFC-245cb and hydrogen fluoride; b) subjecting said reaction product composition to a first distillation step to form a first distillate composition comprising an azeotrope or near-azeotrope composition containing HFC-1234yf and HF and a first bottoms composition comprising HFC-245cb; c) subjecting said first distillate composition to a second distillation step from which a composition enriched in either (i) hydrogen fluoride or (ii) HFC-1234yf is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (c) is removed as a third distillate composition with a third bottoms composition enriched in the same component that was enriched in the second distillate composition.

A further aspect relates to a process for the manufacture of $CF_3CF=CH_2$ (HFC-1234yf) comprising feeding $CF_3CF_2CH_3$ (HFC-245cb) to a dehydrofluorination reaction zone to produce a reaction mixture comprising $CF_3CF=CH_2$ (HFC-1234yf) and hydrogen fluoride.

A further aspect relates to a process for the manufacture of $CF_3CF=CH_2$ (HFC-1234yf) comprising feeding $CF_3CF_2CH_3$ (HFC-245cb) to a dehydrofluorination reaction zone to produce a reaction mixture comprising $CF_3CF=CH_2$ (HFC-1234yf) and hydrogen fluoride.

A further aspect relates to a process for the manufacture of $CF_3CF=CH_2$ (HFC-1234yf) comprising feeding $CF_3CF_2CH_3$ (HFC-245cb) to a dehydrofluorination reaction zone in the presence of catalyst to produce a reaction mixture comprising $CF_3CF=CH_2$ (HFC-1234yf).

A further aspect relates to a process for the manufacture of $CF_3CF=CH_2$ (HFC-1234yf) comprising feeding $CF_3CF_2CH_3$ (HFC-245cb) to a dehydrofluorination reaction zone at elevated temperature in the absence of catalyst to produce a reaction mixture comprising $CF_3CF=CH_2$ (HFC-1234yf) and hydrogen fluoride.

DETAILED DESCRIPTION OF THE INVENTION

One aspect relates to compositions containing 2,3,3,3-tetrafluoropropene (HFC-1234yf, $CF_3CF=CH_2$, CAS reg. no.

754-12-1). HFC-1234yf may be prepared by methods known in the art or as described herein.

Anhydrous hydrogen fluoride (HF) has CAS reg. no. 7664-39-3 and is commercially available.

Also useful in the processes disclosed herein is 1,1,1,2,2-pentafluoropropane (HFC-245cb, $CF_3CF_2CH_3$, CAS reg. no. 1814-88-6). HFC-245cb is available commercially or may be prepared by methods known in the art.

A further aspect provides a process for the manufacture of $CF_3CF=CH_2$ (HFC-1234yf) comprising feeding $CF_3CF_2CH_3$ (HFC-245cb) to a dehydrofluorination reaction zone to produce a reaction mixture comprising $CF_3CF=CH_2$ (HFC-1234yf) and hydrogen fluoride.

A further aspect provides a process for the manufacture of $CF_3CF=CH_2$ (HFC-1234yf) comprising feeding $CF_3CF_2CH_3$ (HFC-245cb) to a dehydrofluorination reaction zone in the presence of catalyst to produce a reaction mixture comprising $CF_3CF=CH_2$ (HFC-1234yf).

In this embodiment, the vapor phase dehydrofluorination of $CF_3CF_2CH_3$ (HFC-245cb) in a reaction zone may be suitably carried out using typical dehydrofluorination catalysts. Generally, the present dehydrofluorination may be carried out using any dehydrofluorination catalyst known in the art. These catalysts include, but are not limited to, aluminum fluoride, fluorided alumina, metals on aluminum fluoride, metals on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, and cubic chromium trifluoride; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof.

Dehydrofluorination catalysts include, but are not limited to, aluminum fluoride, fluorided alumina, metals on aluminumum fluoride, and metals on fluorided alumina, as disclosed in U.S. Pat. No. 5,396,000, incorporated herein by reference. Fluorided alumina and aluminum fluoride can be prepared as described in U.S. Pat. No. 4,902,838, incorporated herein by reference. Suitable metals include chromium, magnesium (e.g., magnesium fluoride), Group VIIB metals (e.g., manganese), Group IIIB methals (e.g., lanthanum), and zinc. In use, such metals are normally present as halides (e.g., fluorides), as oxides and/or as oxyhalides. Metals on aluminum fluoride and metals on fluorided alumina can be prepared by procedures as described in U.S. Pat. No. 4,766,260, incorporated herein by reference. In one embodiment, when supported metals are used, the total metal content of the catalyst is from about 0.1 to 20 percent by weight, typically from about 0.1 to 10 percent by weight. In one embodiment, catalysts include catalysts consisting essentially of aluminum fluoride and/or fluorided alumina.

Additionally, dehydrofluorination catalysts include, but are not limited to, oxides, fluorides, and oxyfluorides of magnesium, zinc and mixtures of magnesium and zinc and/or aluminum. A suitable catalyst may be prepared, for example, by drying magnesium oxide until essentially all water is removed, e.g., for about 18 hours at about 100° C. The dried material is then transferred to the reactor to be used. The temperature is then gradually increased to about 400° C. while maintaining a flow of nitrogen through the reactor to remove any remaining traces of moisture from the magnesium oxide and the reactor. The temperature is then lowered to about 200° C. and a fluoriding agent, such as HF, or other vaporizable fluorine containing compounds such as $SF_4$, $CCl_3F$, $CCl_2F_2$, $CHF_3$ or $CCl_2FCClF_2$, optionally diluted with an inert gas such as nitrogen, is passed through the reactor. The inert gas or nitrogen can be gradually reduced until only HF or other vaporizable fluorine containing compounds is being passed through the reactor. At this point, the temperature can be increased to about 450° C. and held at that temperature to convert the magnesium oxide to a fluoride content corresponding to at least 40 percent by weight, e.g., for 15 to 300 minutes, depending on the fluoriding agent flowrate and the catalyst volume. The fluorides are in the form of magnesium fluoride or magnesium oxyfluoride; the remainder of the catalyst is magnesium oxide. It is understood in the art that fluoriding conditions such as time and temperature can be adjusted to provide higher than 40 percent by weight fluoride-containing material.

Another suitable procedure for the catalyst preparation is to add ammonium hydroxide to a solution of magnesium nitrate and, if present, zinc nitrate and/or aluminum nitrate. The ammonium hydroxide is added to the nitrate solution to a pH of about 9.0 to 9.5. At the end of the addition, the solution is filtered, the solid obtained is washed with water, dried and slowly heated to 500° C., where it is calcined. The calcined product is then treated with a suitable fluorine-containing compound as described above.

Yet another procedure for the preparation of metal (i.e., magnesium, optionally containing also zinc and/or aluminum) fluoride catalysts containing one or more metal fluorides is to treat an aqueous solution of the metal(s) halide(s) or nitrate(s) in deionized water with 48 percent aqueous HF with stirring. Stirring is continued overnight, and the slurry evaporated to dryness on a steam bath. The dried solid is then calcined in air at 400° C. for about four hours, cooled to room temperature, crushed and sieved to provide material for use in catalyst evaluations.

Additionally, dehydrofluorination catalysts include, but are not limited to, lanthanum oxide and fluorided lanthanum oxide.

Suitable fluorided lanthanum oxide compositions may be prepared in any manner analogous to those known to the art for the preparation of fluorided alumina. For example, the catalyst composition can be prepared by fluorination of lanthanum oxide.

Suitable catalyst compositions may also be prepared by precipitation of lanthanum as the hydroxide, which is thereafter dried and calcined to form an oxide, a technique well known to the art. The resulting oxide can then be pretreated as described herein.

The catalyst composition can be fluorinated to the desired fluorine content by pretreatment with a fluorine-containing compound at elevated temperatures, e.g., at about 200° C. to about 450° C. The pretreatment with a vaporizable fluorine-containing compound such as HF, $SF_4$, $CCl_3F$, $CCl_2F_3$, $CHF_3$, $CHClF_2$ or $CCl_2FCClF_2$ can be done in any convenient manner including in the reactor which is to be used for carrying out the dehydrofluorination reaction. By vaporizable fluorine-containing compound is meant a fluorine-containing compound which, when passed over the catalyst at the indicated conditions, will fluorinate the catalyst to the desired degree.

A suitable catalyst may be prepared, for example by drying $La_2O_3$ essentially until all moisture is removed, e.g., for about 18 hours at about 400° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and the vaporizable fluorine-containing compound is passed through the reactor. If necessary, nitrogen or other inert gases can be used as diluents. The $N_2$ or other inert diluents can be gradually reduced until only the vaporizable fluorine-containing compound is being passed through the reactor. At this point the temperature can be increased to about 450° C. and held at that temperature to convert the $La_2O_3$ to a fluorine content corresponding to at least 80 percent $LaF_3$ by weight, e.g., for 15 to 300 minutes, depending on the flow of the fluorine containing compound and the catalyst volume.

Another suitable procedure for the catalyst preparation is to add ammonium hydroxide to a solution of $La(NO_3)_3 6H_2O$. The ammonium hydroxide is added to the nitrate solution to a pH of about 9.0 to 9.5. At the end of the addition, the solution is filtered, the solid obtained is washed with water, and slowly heated to about 400° C., where it is calcined. The calcined product is then treated with a suitable vaporizable fluorine-containing compound as described above.

Additionally, dehydrofluorination catalysts include, but are not limited to, chromium oxides, fluorided chromium oxides, and cubic chromium trifluoride. Cubic chromium trifluoride may be prepared from $CrF_3XH_2O$, where X is 3 to 9, preferably 4, by heating in air or an inert atmosphere (e.g., nitrogen or argon) at a temperature of about 350° C. to about 400° C. for 3 to 12 hours, preferably 3 to 6 hours.

Cubic chromium trifluoride is useful by itself, or together with other chromium compounds, as a dehydrofluorination catalyst. Of note are catalyst compositions comprising chromium wherein at least 10 weight percent of the chromium is in the form of cubic chromium trifluoride, particularly catalyst compositions wherein at least 25 percent of the chromium is in the form of cubic chromium trifluoride, and especially catalyst compositions wherein at least 60 percent of the chromium is in the form of cubic chromium trifluoride. The chromium, including the cubic chromium trifluoride can be supported on and/or physically mixed with materials such as carbon, aluminum fluoride, fluorided alumina, lanthanum fluoride, magnesium fluoride, calcium fluoride, zinc fluoride and the like. Preferred are combinations including cubic chromium trifluoride in combination with magnesium fluoride and/or zinc fluoride.

Additionally, dehydrofluorination catalysts include, but are not limited to, activated carbon, or three dimensional matrix carbonaceous materials as disclosed in U.S. Pat. No. 6,369,284, incorporated herein by reference; or carbon or metals such as, for example, sodium, potassium, rubidium, cesium, yttrium, lanthanum, cerium, praseodymium, neodymium, samarium, chromium, iron, cobalt, rhodium, nickel, copper, zinc, and mixtures thereof, supported on carbon as disclosed in U.S. Pat No. 5,268,122, incorporated herein by reference. Carbon from any of the following sources are useful for the process of this invention; wood, peat, coal, coconut shells, bones, lignite, petroleum-based residues and sugar. Commercially available carbons which may be used in this invention include those sold under the following trademarks: Barneby & Sutcliffe™, Darco™, Nucharm, Columbia JXN™, Columbia LCK™, Calgon PCB, Calgon BPL™, Westvaco™, Norit™, and Barnaby Cheny NB™.

Carbon includes acid-washed carbon (e.g., carbon which has been treated with hydrochloric acid or hydrochloric acid followed by hydrofluoric acid). Acid treatment is typically sufficient to provide carbon that contains less than 1000 ppm of ash. Suitable acid treatment of carbon is described in U.S. Pat. No. 5,136,113, incorporated herein by reference. The carbon of this invention also includes three dimensional matrix porous carbonaceous materials. Examples are those described in U.S. Pat. No. 4,978,649, incorporated herein by reference. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

The physical shape of the catalyst is not critical and may, for example, include pellets, powders or granules. Additionally, for catalysts supported on carbon, the carbon may be in the form of powder, granules, or pellets, or the like. Although not essential, catalysts that have not been fluorided may be treated with HF before use. It is thought that this converts some of the surface oxides to oxyfluorides. This pretreatment can be accomplished by placing the catalyst in a suitable container (which can be the reactor to be used to perform a reaction disclosed herein) and thereafter, passing HF over the dried catalyst so as to partially saturate the catalyst with HF. This is conveniently carried out by passing HF over the catalyst for a period of time (e.g., about 15 to 300 minutes) at a temperature of, for example, about 200° C. to about 450° C.

The catalytic dehydrofluorination may be suitably conducted at a temperature in the range, in one embodiment, of from about 200° C. to about 500° C., and, in another embodiment, from about 300° C. to about 450° C. The contact time is typically, in one embodiment, from about 1 to about 450 seconds and, in another embodiment, from about 10 to about 120 seconds.

The reaction pressure can be subatmospheric, atmospheric or superatmostpheric. Generally, near atmospheric pressures are preferred. However, the dehydrofluorination can be beneficially run under reduced pressure (i.e., pressures less than one atmosphere).

The catalytic dehydrofluorination can optionally be carried out in the presence of an inert gas such as nitrogen, helium, or argon. The addition of an inert gas can be used to increase the extent of dehydrofluorination. Of note are processes where the mole ratio of inert gas to $CF_3CF_2CH_3$ (HFC-245cb) undergoing dehydrofluorination is from about 5:1 to about 1:1. Nitrogen is the preferred inert gas.

A further aspect provides a process for the manufacture of $CF_3CF=CH_2$ (HFC-1234yf) comprising feeding $CF_3CF_2CH_3$ (HFC-245cb) to a dehydrofluorination reaction zone at elevated temperature in the absence of catalyst to produce a reaction mixture comprising $CF_3CF=CH_2$ (HFC-1234yf) and hydrogen fluoride.

In the present embodiment of dehydrofluorination, the dehydrofluorination of $CF_3CF_2CH_3$ (HFC-245cb) can be carried out in a reaction zone at an elevated temperature in the absence of a catalyst as disclosed in U.S. Provisional Patent Application No. 60/623,210 filed Oct. 29, 2004, incorporated herein by reference. Appropriate temperatures may be between about 350° C. and about 900° C., and, in another embodiment, between about 450° C. and about 900° C. The residence time of gases in the reaction zone is typically, in one embodiment, from about 0.5 to about 60 seconds, and, in another embodiment, from about 2 seconds to about 20 seconds.

The reaction pressure for the dehydrofluorination reaction at elevated temperature in the absence of catalyst may be subatmospheric, atmospheric, or superatmospheric. Generally, near atmospheric pressures are preferred. However, the dehydrofluorination can be beneficially run under reduced pressure (i.e., pressures less than one atmosphere).

The dehydrofluorination at an elevated temperature in the absence of a catalyst may optionally be carried out in the presence of an inert gas such as nitrogen, helium or argon. The addition of an inert gas can be used to increase the extent of dehydrofluorination. Of note are processes where the mole ratio of inert gas to the $CF_3CF_2CH_3$ undergoing dehydrofluorination is from about 5:1 to about 1:1. Nitrogen is the preferred inert gas.

The reaction zone for either catalyzed or non-catalyzed dehydrofluorination may be a reaction vessel fabricated from nickel, iron, titanium or their alloys, as described in U.S. Pat. No. 6,540,933, incorporated herein by reference. A reaction vessel of these materials (e.g., a metal tube) optionally packed with the metal in suitable form may also be used. When reference is made to alloys, it is meant a nickel alloy containing from about 1 to about 99.9 weight percent nickel, an iron alloy containing about 0.2 to about 99.8 weight percent iron, and a titanium alloy containing about 72 to about 99.8 weight percent titanium. Of note is the use of an empty (unpacked) reaction vessel made of nickel or alloys of nickel such as those containing about 40 weight percent to about 80 weight percent nickel, e.g., Inconel™ 600 nickel alloy, Hastelloy™ C617 nickel alloy or Hastelloy™ C276 nickel alloy.

When used for packing, the metal or metal alloys may be particles or formed shapes such as perforated plates, rings, wire, screen, chips, pipe, shot, gauze, or wool.

In considering a process for the dehydrofluorination of HFC-245cb to HFC-1234yf and HF and the isolation of HFC-1234yf from such a process, it has been discovered surprisingly that the hydrofluoroolefin HFC-1234yf forms an azeotrope with HF.

One aspect provides a composition, which comprises HFC-1234yf and an effective amount of hydrogen fluoride (HF) to form an azeotrope composition. By effective amount is meant an amount, which, when combined with HFC-1234yf, results in the formation of an azeotrope or near-azeotrope mixture. As recognized in the art, an azeotrope or a near-azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

For the purpose of this discussion, near-azeotrope composition (also commonly referred to as an "azeotrope-like composition") means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotrope compositions in which during boiling or evaporation, the liquid composition changes to a substantial degree.

Additionally, near-azeotrope compositions exhibit dew point pressure and bubble point pressure with virtually no pressure differential. That is to say that the difference in the dew point pressure and bubble point pressure at a given temperature will be a small value. It may be stated that compositions with a difference in dew point pressure and bubble point pressure of less than or equal to 3 percent (based upon the bubble point pressure) may be considered to be a near-azeotrope.

Accordingly, the essential features of an azeotrope or a near-azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope or near-azeotrope liquid composition is subjected to boiling at different pressures. Thus, an azeotrope or a near-azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

Compositions may be formed that comprise azeotrope combinations of hydrogen fluoride with HFC-1234yf. These include compositions comprising from about 19.3 mole percent to about 31.1 mole percent HF and from about 80.7 mole percent to about 68.9 mole percent HFC-1234yf (which forms an azeotrope boiling at a temperature from between about −20° C. and about 80° C. and at a pressure from between about 23.2 psi (160 kPa) and about 453 psi (3123 kPa).

Additionally, near-azeotrope compositions containing HF and HFC-1234yf may also be formed. Such near-azeotrope compositions comprise about 64.6 mole percent to about 92.4 mole percent HFC-1234yf and about 35.4 mole percent to about 7.6 mole percent HF at temperatures ranging from about −20° C. to about 80° C. and at pressures from about 23.2 psi (160 kPa) and about 453 psi (3123 kPa).

It should be understood that while an azeotrope or near-azeotrope composition may exist at a particular ratio of the components at given temperatures and pressures, the azeotrope composition may also exist in compositions containing other components.

Compositions may be formed that consist essentially of azeotrope combinations of hydrogen fluoride with HFC-1234yf. These include compositions consisting essentially of from about 19.3 mole percent to about 31.1 mole percent HF and from about 80.7 mole percent to about 68.9 mole percent HFC-1234yf (which forms an azeotrope boiling at a temperature from between about −20° C. and about 80° C. and at a pressure from between about 23.2 psi (160 kPa) and about 453 psi (3123kPa).

Near azeotrope compositions may also be formed that consist essentially of about 64.6 mole percent to about 92.4 mole percent HFC-1234yf and about 35.4 mole percent to about 7.6 mole percent HF at temperatures ranging from about −20° C. to about 80° C. and at pressures from about 23.2 psi (160 kPa) and about 453 psi (3123 kPa).

At atmospheric pressure, the boiling points of hydrofluoric acid and HFC-1234yf are about 19.5° C. and −28.3° C., respectively. The relative volatility at 67.6 psi (466 kPa) and 9.3° C. of HF and HFC-1234yf was found to be nearly 1.0 as 24.4 mole percent HF and 75.6 mole percent HFC-1234yf was approached. The relative volatility at 187 psi (1289 kPa) and 44.4° C. was found to be nearly 1.0 as 28.0 mole percent HF and 72.0 mole percent HFC-1234yf was approached. These data indicate that the use of conventional distillation procedures will not result in the separation of a substantially pure compound because of the low value of relative volatility of the compounds.

To determine the relative volatility of HF with HFC-1234yf, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", $4^{th}$ Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and HFC-1234yf behave in an ideal manner, and can sufficiently predict the relative volatilities of the components in such mixtures. Thus, while HF has a good relative volatility compared to HFC-1234yf at low HFC-1234yf concentrations, the relative volatility becomes nearly 1.0 as 75.6 mole percent HFC-1234yf was approached at 9.3° C. This would make it impossible to separate HFC-1234yf from HF by conventional distillation from such a mixture. Where the relative volatility approaches 1.0 defines the system as forming a near-azeotrope or azeotrope composition.

It has been found that azeotropes of HFC-1234yf and HF are formed at a variety of temperatures and pressures. Azeotrope compositions may be formed between 23.2 psi (160 kPa) at a temperature of −20° C. and 453 psi (3121 kPa) at a temperature of 80° C. said compositions consisting essentially of HFC-1234yf and HF range from about 19.3 mole percent HF (and 80.7 mole percent HFC-1234yf) to about 31.1 mole percent HF (and 68.9 mole percent HFC-1234yf). An azeotrope of HF and HFC-1234yf has been found at 9.3° C. and 67.6 psi (466 kPa) consisting essentially of about 24.4 mole percent HF and about 75.6 mole percent HFC-1234yf. An azeotrope of HF and HFC-1234yf has also been found at 44.4° C. and 187 psi (1289 kPa) consisting essentially of about 28.0 mole percent HF and about 72.0 mole percent HFC-1234yf. Based upon the above findings, azeotrope compositions at other temperatures and pressures may be calculated. It has been calculated that an azeotrope composition of about 19.3 mole percent HF and about 80.7 mole percent HFC-1234yf can be formed at −20° C. and 23.2 psi (160 kPa) and an azeotrope composition of about 31.1 mole percent HF and about 68.9 mole percent HFC-1234yf can be formed at 80° C. and 453 psi (3121 kPa). Accordingly, one aspect provides an azeotrope composition consisting essentially of from about 19.3 mole percent to about 31.1 mole percent HF and from about 80.7 mole percent to about 68.9 mole percent HFC-1234yf, said composition having a boiling point of about −20° C. at 23.2 psi (160 kPa) to about 80° C. at 453 psi (3121 kPa).

It has also been found that azeotrope or near-azeotrope compositions may be formed between about 23.2 psi (160 kPa) to about 453 psi (3121 kPa) at temperatures ranging from about −20° C. to about 80° C., said compositions consisting essentially of about 64.6 mole percent to about 92.4 mole percent HFC-1234yf and about 35.4 mole percent to about 7.6 mole percent HF.

The HF/HFC-1234yf azeotrope and near-azeotrope compositions are useful in processes to produce HFC-1234yf and in processes to purify HFC-1234yf. In fact, the HF/HFC-1234yf azeotrope and near-azeotrope compositions may be useful in any process that creates a composition containing HFC-1234yf and HF.

Azeotropic distillation may be carried out to separate HFC-1234yf from HFC-245cb, which is the starting material for production of HFC-1234yf, by vapor phase dehydrofluorination. A two-column azeotropic distillation may then be carried out to separate the co-produced HF from the desired HFC-1234yf product. HF may be removed from the halogenated hydrocarbon components of the product mixture using, for example, standard aqueous solution scrubbing techniques. However, the production of substantial amounts of scrubbing discharge can create aqueous waste disposal concerns. Thus, there remains a need for processes utilizing HF from such product mixtures.

While the initial mixture treated in accordance with the processes disclosed herein can be obtained from a variety of sources, including but not limited to the addition of HFC-1234yf to HF-containing compositions, an advantageous use of the present processes resides in treating the effluent mixtures from the preparation of HFC-1234yf.

HFC-1234yf may be prepared by the vapor phase dehydrofluorination of HFC-245cb as described earlier herein.

A further aspect provides a process for the separation of HFC-1234yf from HFC-245cb comprising: a) forming a mixture of HFC-1234yf, HFC-245cb, and hydrogen fluoride; and b) subjecting said mixture to a distillation step forming a column distillate composition comprising an azeotrope or near-azeotrope composition of HF and HFC-1234yf essentially free of HFC-245cb. The present inventive process may optionally further comprise forming a column-bottoms composition comprising HFC-245cb.

As described herein, by "essentially free of HFC-245cb" is meant that the composition contains less than about 100 ppm (mole basis), preferably less than about 10 ppm and most preferably less than about 1 ppm, of HFC-245cb.

This azeotropic distillation takes advantage of the low boiling azeotrope composition formed by HFC-1234yf and HF. The azeotrope composition boils at a temperature lower than the boiling point of either pure component and lower than the boiling point of HFC-245cb as well.

As stated previously, the mixture of HFC-1234yf, HFC-245cb and HF may be formed by any practical means. Generally, the present process is particularly useful for the separation of HFC-1234yf from the reaction mixture produced by the dehydrofluorination of HFC-245cb. HF is a co-product formed in this dehydrofluorination reaction. The reaction mixture produced may then be treated by the instant process to remove HFC-245cb. The HFC-1234yf is taken overhead as the distillate from the distillation column as an azeotrope or near-azeotrope composition of HFC-1234yf with HF. The HFC-245cb may be taken out of the bottom of the column as a bottoms composition and may contain some amount of HF, as well. The amount of HF in the HFC-245cb from the bottom of the distillation column may vary from about 35 mole percent to less than 1 part per million (ppm, mole basis) depending on the manner in which the dehydrofluorination reaction is conducted. In fact, if the dehydrofluorination reaction is conducted in a manner to provide 50 percent conversion of the HFC-245cb and the reaction mixture leaving the reaction zone is fed directly to the distillation step, the HFC-245cb leaving the bottom of the distillation process will contain about 43 mole percent HF.

In one embodiment, operating the present azeotropic distillation involves providing an excess of HFC-1234yf to the distillation column. If the proper amount of HFC-1234yf is fed to the column, then all the HF may be taken overhead as an azeotrope composition containing HFC-1234yf and HF. Thus, the HFC-245cb removed from the column bottoms will be essentially free of HF.

As described herein, by "essentially free of HF" is meant that the composition contains less than about 100 ppm (mole basis), preferably less than about 10 ppm and most preferably less than about 1 ppm, of HF.

In the distillation step, the distillate exiting the distillation column overhead comprising HF and HFC-1234yf may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step depend upon a number of parameters, such as the diameter of the distillation column, feed points, and the number of separation stages in the column, among others. The operating pressure of the distillation column may range from about 10 psi pressure to about 200 psi (1380 kPa), normally about 20 psi to about 50 psi. The distillation column is typically operated at a pressure of about 25 psi (172 kPa) with a bottoms temperature of about $-3°$ C. and a tops temperature of about $-17°$ C. Normally, increasing the reflux ratio results in increased distillate stream purity, but generally the reflux ratio ranges between 1/1 to 200/1. The temperature of the condenser, which is located adjacent to the top of the column, is normally sufficient to substantially fully condense the distillate that is exiting from the top of the column, or is that temperature required to achieve the desired reflux ratio by partial condensation.

The column distillate composition comprising an azeotrope or near-azeotrope composition of HF and HFC-1234yf, essentially free of HFC-245cb, must be treated to remove the HF and provide pure HFC-1234yf as product. This may be accomplished, for example, by neutralization or by a second distillation process, as described herein.

A further aspect provides a process for the separation of HFC-1234yf from a mixture comprising an azeotrope or near-azeotrope composition of HFC-1234yf and HF, said process comprising: a) subjecting said mixture to a first distillation step in which a composition enriched in either (i) hydrogen fluoride or (ii) HFC-1234yf is removed as a first distillate composition with a first bottoms composition being enriched in the other of said components (i) or (ii); and b) subjecting said first distillate composition to a second distillation step conducted at a different pressure than the first distillation step in which the component enriched as first bottoms composition in (a) is removed as a second distillate composition with the bottoms composition of the second distillation step enriched in the same component which was enriched in the first distillate composition.

The process as described above takes advantage of the change in azeotropic composition at different pressures to effectuate the separation of HFC-1234yf and HF. The first distillation step may be carried out at high pressure relative to the second distillation step. At higher pressures, the HF/HFC-1234yf azeotrope contains less HFC-1234yf. Thus, this high-pressure distillation step produces an excess of HFC-1234yf, which boiling at a higher temperature than the azeotrope will exit the column as the bottoms as pure HFC-1234yf. The first column distillate is then fed to a second distillation step operating at lower pressure. At the lower pressure, the HF/HFC-1234yf azeotrope shifts to lower concentrations of HF. Therefore, in this second distillation step, there exists an excess of HF. The excess HF, having a boiling point higher than the azeotrope, exits the second distillation column as the bottoms composition. The present process may be conducted in such as manner as to produce HFC-1234yf essentially free of HF. Additionally, the present process may be conducted in such a manner as to produce HF essentially free of HFC-1234yf.

Alternatively, the first distillation step may be carried out at low pressure relative to the second distillation step. At lower pressures, the HF/HFC-1234yf azeotrope contains less HF. Thus, this low-pressure distillation step produces an excess of HF, which boiling at a higher temperature than the azeotrope will exit the column as the bottoms as pure HF. The first column distillate is then fed to a second distillation step operating at higher pressure. At the higher pressure, the HF/HFC-1234yf azeotrope shifts to lower concentrations of HFC-1234yf. Therefore, in this second distillation step, there exists an excess of HFC-1234yf. The excess HFC-1234yf, having a boiling point higher than the azeotrope, exits the second distillation column as the bottoms composition. The present process may be conducted in such as manner as to produce HFC-1234yf essentially free of HF. Additionally, the present process may be conducted in such a manner as to produce HF essentially free of HFC-1234yf.

As described herein, by "essentially free of HFC-1234yf" is meant that the composition contains less than about 100 ppm (mole basis), preferably less than about 10 ppm and most preferably less than about 1 ppm, of HFC-1234yf.

The endothermic dehydrofluorination reaction of HFC-245cb to produce HFC-1234yf may be accomplished, for example, in a tubular reactor with catalyst in the tubes and with a heating medium on the shellside of the reactor. Alternatively, a heat carrier may be used to permit adiabatic operation. Either pure HFC-245cb or pure HFC-1234yf, both being produced by the distillation processes described herein, may be recycled back to the reactor to serve as heat carrier. HFC-245cb would be a preferred heat carrier, as introduction of HFC-1234yf to the dehydrofluorination reactor will result in a reduction in single-pass conversion of HFC-245cb.

In both the first and second distillation steps, the distillate exiting the distillation column overhead comprising HF and HFC-1234yf may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step of the present invention depend upon a number of parameters, such as the diameter of the distillation column, feed points, and the number of separation stages in the column, among others. The operating pressure of the high pressure distillation column (whether high pressure is the first distillation column or the second distillation column) may range from about 200 psi (1380 kPa) pressure to about 500 psi (3450 kPa), normally about 250 psi (1724 kPa) to about 400 psi (2760 kPa). The first distillation column is typically operated at a pressure of about 365 psi (2517 kPa) with a bottoms temperature of about 80° C. and a tops temperature of about 71° C. Normally, increasing the reflux ratio results in increased distillate stream purity, but generally the reflux ratio ranges between 0.1/1 to 100/1. The temperature of the condenser, which is located adjacent to the top of the column, is normally sufficient to substantially fully condense the distillate that is exiting from the top of the column, or is that temperature required to achieve the desired reflux ratio by partial condensation.

The operating pressure of the low pressure distillation column (whether low pressure is the first distillation column or the second distillation column) may range from about 5 psi (34 kPa) pressure to about 50 psi (345 kPa), normally about 5 psi (34 kPa) to about 20 psi (138 kPa). The low pressure distillation column is typically operated at a pressure of about 25 psi (172 kPa) with a bottoms temperature of about 37° C. and a tops temperature of about −18° C. Normally, increasing the reflux ratio results in increased distillate stream purity, but generally the reflux ratio ranges between 0.1/1 to 50/1. The temperature of the condenser, which is located adjacent to the top of the column, is normally sufficient to substantially fully condense the distillate that is exiting from the top of the column, or is that temperature required to achieve the desired reflux ratio by partial condensation.

Figure 1:
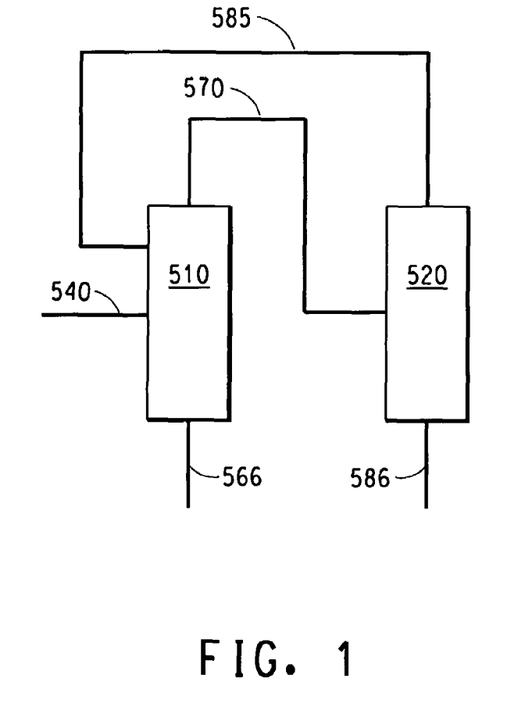
FIG. 1 is a schematic flow diagram illustrating one embodiment for practicing a two-column azeotropic distillation process.

FIG. 1 is illustrative of one embodiment for practicing the present two-column distillation process for the separation of HFC-1234yf and HF. Referring to FIG. 1, a feed mixture derived from a prior azeotropic distillation comprising HF and HFC-1234yf, wherein the molar ratio of HF:HFC-1234yf is about 0.25:1 (or lower), is passed through line (540) to a multiple stage distillation column (510), operating at a temperature of about 71° C. and a pressure of about 365 psi (2517 kPa). The bottoms of the distillation column (510), containing essentially pure HFC-1234yf at a temperature of about 80° C. and a pressure of about 367 psi (2530 kPa) is removed from the bottom of column (510) through line (566). The distillate from column (510), containing the HF/HFC-1234yf azeotrope (HF:HFC-1234yf molar ratio is about 0.43:1) at a temperature of about 71° C. and a pressure of about 365 psi (2517 kPa) is removed from the top of column (510) and sent through line (570) to a multiple stage distillation column (520). The distillate from column (520), containing the HF/HFC-1234yf azeotrope (molar ratio is about 0.25:1) at a temperature of about −18° C. and a pressure of about 25 psi (172 kPa), is removed from column (520) through line (585) and is recycled back to column (510). The bottoms of column (520) containing essentially pure HF at a temperature of about 37° C. and a pressure of about 27 psi (186 kPa) is removed through line (586).

A further aspect provides a process for the purification of HFC-1234yf from a mixture of HFC-1234yf, HFC-245cb, and HF, said process comprising: a) subjecting said mixture to a first distillation step to form a first distillate comprising an azeotrope or near-azeotrope composition containing HFC-1234yf and HF and a first bottoms comprising HFC-245cb; b) subjecting said first distillate to a second distillation step from which a composition enriched in either (i) hydrogen fluoride or (ii) HFC-1234yf is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed as a second distillate composition with the bottoms composition of the second distillation step enriched in the same component that was enriched in the first distillate composition.

A further aspect provides a process to produce HFC-1234yf comprising: a) feeding HFC-245cb to a reaction zone for dehydrofluorination to form a reaction product composition comprising HFC-1234yf, unreacted HFC-245cb and hydrogen fluoride; b) subjecting said reaction product composition to a first distillation step to form a first distillate composition comprising an azeotrope or near-azeotrope composition containing HFC-1234yf and HF and a first bottoms composition comprising HFC-245cb; c) subjecting said first distillate composition to a second distillation step from which a composition enriched in either (i) hydrogen fluoride or (ii) HFC-1234yf is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (c) is removed as a third distillate composition with the bottoms composition of the third distillation step enriched in the same component that was enriched in the second distillate composition. Optionally, the process may further comprise recycling at least some portion of said first bottoms (HFC-245cb) to said reaction zone. Optionally, the process may further comprise recycling at least some portion of said second bottoms composition or said third bottoms composition to said reaction zone. Optionally, the process may further comprise recycling at least some portion of said second bottoms composition or said third bottoms composition to said first distillation step. Optionally, the process may further comprise recovering at least some portion of said HFC-1234yf essentially free of HFC-245cb and HF.

As described herein, by "essentially free of HFC-245cb and HF" is meant that the composition contains less than about 100 ppm (mole basis), preferably less than about 10 ppm and most preferably less than about 1 ppm, of each of HFC-245cb and HF.

The reaction zone and conditions for the dehydrofluorination reaction have been described previously herein.

Figure 2:
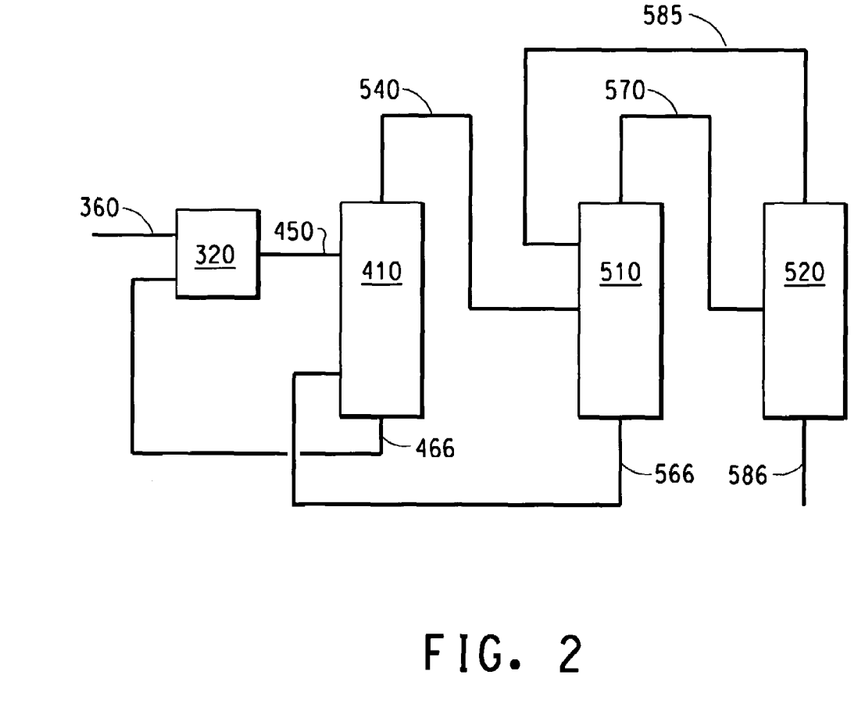
FIG. 2 is a schematic flow diagram illustrating one embodiment for practicing a process for production of HFC-1234yf.

FIG. 2 is illustrative of one embodiment for practicing the present process for production of HFC-1234yf. HFC-245cb is fed through line (360) to reactor (320). The reactor effluent mixture comprising HF, HFC-245cb and HFC-1234yf, exits the reactor through line (450) and is fed to a multiple stage distillation column (410). The bottoms of distillation column (410), containing essentially pure HFC-245cb is removed from the bottom of column (410) through line (466) and may be recycled back to the reactor. The distillate from column (410), containing the HF/HFC-1234yf azeotrope is removed from the top of column (410) and is sent through line (540) to a second multiple stage distillation column (510). The bottoms from column (510), which is essentially pure HFC-1234yf, is removed from column (510) through line (566) and may be recycled back to the reactor (320) as a heat carrier. The distillate from column (510), containing the HF/HFC-1234yf azeotrope, is fed through line (570) to a third multiple stage distillation column (520). The distillate from column (520) comprising HF/HFC-1234yf is removed through line (585) and may be recycled to the second distillation column (510). The bottoms composition from column (520) is essentially pure HF and is removed from column (520) through line (586). The essentially pure HF product from this process may be used in any manner appropriate such as feeding to a fluorination reactor for production of a fluorochemical compound, or may be neutralized for disposal.

While not illustrated in the figures, it is understood that certain pieces of process equipment may be used in the processes described herein, for optimization. For instance, pumps, heaters or coolers may be used where appropriate. As an example, it is desirable to have the feed to a distillation column at the same temperature as the point in the column that it is fed. Therefore, heating or cooling of the process stream may be necessary to match the temperature.

Without further elaboration, it is believed that one skilled in the art can, using the description herein, utilize the disclosed compositions and processes to their fullest extent. The following exemplary embodiments are, therefore, to be construed as merely illustrative, and do not constrain the remainder of the disclosure in any way whatsoever.

EXAMPLES

Example 1

Synthesis of HFC-1234yf By Dehydrofluorination with Fluorided Alumina Catalyst

A Hastelloy tube reactor (1.0" OD×0.854" ID×9.5" L) was filled with 25 cc of gamma-alumina ground to 12-20 mesh. The packed portion of the reactor was heated by a 5"×1" ceramic band heater clamped to the outside of the reactor. A thermocouple, positioned between the reactor wall and the heater measured the reactor temperature. The catalyst was dried by heating at 200° C. for 15 minutes under a nitrogen purge and then reacted with a HF/$N_2$ mixture heated up to 425° C. to yield 16.7 gm of activated fluorided alumina.

At a temperature of 350° C., 10 sccm of nitrogen ($1.7 \times 10^{-7}$ m³/s) and 15 sccm ($2.5 \times 10^{-7}$ m³/s) of HFC-245cb ($CF_3CF_2CH_3$) were mixed and flowed through the reactor. The temperature was then raised to 400° C., the flow rates held constant. The effluent for both temperatures was sampled and analyzed by $^{19}F$ NMR. Additionally, the effluent was analyzed by GC/FID to determine concentrations as listed in Table 1.

TABLE 1

| Temp., ° C. | $N_2$ flow (sccm) | HFC-245cb flow (sccm) | Concentrations, (GC/FID area %) | | |
|---|---|---|---|---|---|
| | | | HFC-1234yf | HFC-245cb | Unknowns |
| 350 | 10 | 15 | 84.2 | 12.8 | 3.0 |
| 400 | 10 | 15 | 91.3 | 1.9 | 6.8 |

Example 2

Synthesis of HFC-1234yf with Carbon Catalyst

To a Hastelloy nickel alloy reactor (1.0" OD×0.854" ID×9.5" L) was charged 14.5 g (25 mL) of spherical (8 mesh) three dimensional matrix porous carbonaceous material prepared substantially as described in U.S. Pat. No. 4,978,649, incorporated herein by reference. The packed portion of the reactor was heated by a 5"×1" ceramic band heater clamped to the outside of the reactor. A thermocouple, positioned between the reactor wall and the heater measured the reactor temperature.

At a temperature of 400° C., 10 sccm ($1.7 \times 10^{-7}$ m³/s) of nitrogen and 15 sccm ($2.5 \times 10^{-7}$ m³/s) of HFC-245cb ($CF_3CF_2CH_3$) were mixed and flowed through the reactor giving a contact time of 60 seconds. The flows were then reduced to 5 sccm of nitrogen ($8.3 \times 10^{-8}$ m³/s) and 7.5 sccm ($1.3 \times 10^{-7}$ m³/s) of HFC-245cb ($CF_3CF_2CH_3$) giving a contact time of 120 seconds. The effluent was sampled under both sets of conditions and analyzed by $^{19}F$ NMR. Additionally, the effluent was analyzed by GC/FID to determine concentrations as listed in Table 2.

TABLE 2

| Temp., ° C. | $N_2$ flow (sccm) | HFC-245cb flow (sccm) | Concentrations, (GC area %) | | |
|---|---|---|---|---|---|
| | | | HFC-1234yf | HFC-245cb | Unknowns |
| 400 | 10 | 15 | 6.0 | 93.9 | 0.1 |
| 400 | 5 | 7.5 | 22.8 | 76.4 | 0.8 |

Example 3

Phase Studies of Mixtures of HF and HFC-1234yf

A phase study was performed for a composition consisting essentially of HFC-1234yf and HF, wherein the composition was varied and the vapor pressures were measured at both 9.3° C. and 44.4° C. Based upon the data from the phase studies, azeotrope compositions at other temperature and pressures have been calculated.

Table 3 provides a compilation of experimental and calculated azeotrope compositions for HF and HFC-1234yf at specified temperatures and pressures.

TABLE 3

| Temperature, ° C. | Pressure, psi (kPa) | Mole % HF | Mole % HFC-1234yf |
|---|---|---|---|
| −20 | 23.2 (160) | 19.3 | 80.7 |
| −18.5 | 24.7 (170) | 19.7 | 80.3 |
| 0 | 49.5 (341) | 23.0 | 77.0 |
| 9.3 | 67.6 (466) | 24.4 | 75.6 |
| 20 | 94.6 (652) | 25.7 | 74.3 |
| 40 | 167 (1151) | 27.7 | 72.3 |
| 44.4 | 187 (1289) | 28.0 | 72.0 |
| 60 | 278 (1917) | 29.5 | 70.5 |
| 70 | 354 (2441) | 30.3 | 69.7 |
| 71.2 | 365 (2517) | 30.4 | 69.6 |
| 75 | 400 (2758) | 30.7 | 69.3 |
| 80 | 453 (3123) | 31.1 | 68.9 |

Example 4

Dew Point and Bubble Point Vapor Pressures for HFC-1234yf

The dew point and bubble point vapor pressures for compositions disclosed herein were calculated from measured and calculated thermodynamic properties. The near-azeotrope range is indicated by the minimum and maximum concentration of HFC-1234yf (mole percent, mol %) for which the difference in dew point and bubble point pressures is less than or equal to 3% (based upon bubble point pressure). The results are summarized in Table 4.

TABLE 4

| Temperature, °C. | Azeotrope composition, mol % HFC-1234yf | Near-azeotrope compositions, mol % HFC-1234yf | |
|---|---|---|---|
| | | Minimum | Maximum |
| −20 | 80.7 | 75.0 | 92.4 |
| 40 | 72.4 | 66.4 | 83.4 |
| 80 | 69.0 | 64.6 | 80.6 |

Example 5

Azeotropic Distillation for Separation of HFC-1234vf From HFC-245cb

A mixture of HF, HFC-1234yf, and HFC-245cb is fed to a distillation column for the purpose of purification of HFC-1234yf. The data in Table 5 were obtained by calculation using measured and calculated thermodynamic properties.

TABLE 5

| Component or variable | Column feed | Column overhead (distillate) | Column bottoms |
|---|---|---|---|
| HFC-245cb, mol % | 33.4 | 10 ppm | 57.0 |
| HFC-1234yf, mol % | 33.3 | 80.3 | 280 ppm |
| HF, mol % | 33.3 | 19.7 | 43.0 |
| Temp, °C. | — | −18.5 | −6.0 |
| Pressure, psi (kPa) | — | 24.7 (170) | 26.7 (184) |

Example 6

Azeotropic Distillation for Separation of HFC-1234vf From HFC-245cb

A mixture of HF, HFC-1234yf, and HFC-245cb is fed to a distillation column for the purpose of purification of HFC-1234yf. The data in Table 6 were obtained by calculation using measured and calculated thermodynamic properties.

TABLE 6

| Component or variable | Column feed | Column overhead (distillate) | Column bottoms |
|---|---|---|---|
| HFC-245cb, mol % | 16.3 | 10 ppm | 100 |
| HFC-1234yf, mol % | 67.4 | 80.5 | 50 ppm |
| HF, mol % | 16.3 | 19.5 | — |
| Temp, °C. | — | −17.4 | −2.7 |
| Pressure, psi (kPa) | — | 24.7 (170) | 26.7 (184) |

Example 7

Azeotropic Distillation for Separation of HFC-1234yf from HFC-245cb

A mixture of HF, HFC-1234yf, and HFC-245cb is fed to a distillation column for the purpose of purification of HFC-1234yf. The data in Table 7 were obtained by calculation using measured and calculated thermodynamic properties.

TABLE 7

| Component or variable | Column feed | Column overhead (distillate) | Column bottoms |
|---|---|---|---|
| HFC-245cb, mol % | 27.3 | 10 ppm | 100 |
| HFC-1234yf, mol % | 63.6 | 87.5 | 27 ppm |
| HF, mol % | 9.1 | 12.5 | — |
| Temp, °C. | — | −17.2 | −2.7 |
| Pressure, psi (kPa) | — | 24.7 (170) | 26.7 (184) |

Example 8

Azeotropic Distillation for Separation of HFC-1234yf from HFC-245cb

A mixture of HF, HFC-1234yf, and HFC-245cb is fed to a distillation column for the purpose of purification of HFC-1234yf. The data in Table 8 were obtained by calculation using measured and calculated thermodynamic properties.

TABLE 8

| Component or variable | Column feed | Column overhead (distillate) | Column bottoms |
|---|---|---|---|
| HFC-245cb, mol % | 17.6 | 10 ppm | 100 |
| HFC-1234yf, mol % | 76.5 | 92.9 | 47 ppm |
| HF, mol % | 5.9 | 7.1 | — |
| Temp, °C. | — | −17.1 | −2.7 |
| Pressure, psi (kPa) | — | 24.7 (170) | 26.7 (184) |

Example 9

Two-Column Azeotropic Distillation for Separation of HFC-1234yf from HF

A mixture of HF and HFC-1234yf is fed to a distillation process for the purpose of purification of the HFC-1234yf. The data in Table 9 were obtained by calculation using measured and calculated thermodynamic properties. The numbers at the top of the columns refer to FIG. 1.

TABLE 9

| Compound or variable | 540 Feed Mixture | 570 Column (510) distillate | 566 HFC-1234yf product | 585 Column (520) distillate | 586 HF product |
|---|---|---|---|---|---|
| HF, mol % | 19.8 | 30.0 | — | 20.0 | 100 |
| HFC-1234yf, mol % | 80.2 | 70.0 | 100 | 80.0 | — |
| Temp., °C. | — | 71.2 | 80.2 | −18.4 | 36.9 |
| Pres., psi (kPa) | — | 364.7 (2515) | 366.7 (2528) | 24.7 (170) | 26.7 (184) |

Example 10

Two-column Azeotropic Distillation for Separation of HFC-1234vf from HF

A mixture of HF and HFC-1234yf is fed to a distillation process for the purpose of purification of the HFC-1234yf. The data in Table 10 were obtained by calculation using measured and calculated thermodynamic properties. The numbers at the top of the columns refer to FIG. 1.

TABLE 10

| Compound or variable | 540 Feed Mixture | 570 Column (510) distillate | 566 HFC-1234yf product | 585 Column (520) distillate | 586 HF product |
|---|---|---|---|---|---|
| HF, mol % | 16.0 | 30.0 | — | 20.0 | 100 |
| HFC-1234yf, mol % | 84.0 | 70.0 | 100 | 80.0 | — |
| Temp., ° C. | — | 71.2 | 80.2 | −18.4 | 36.9 |
| Pres., psi (kPa) | — | 364.7 (2515) | 366.7 (2528) | 24.7 (170) | 26.7 (184) |

Example 11

Two-Column Azeotropic Distillation for Separation of HFC-1234vf from HF

A mixture of HF and HFC-1234yf is fed to a distillation process for the purpose of purification of the HFC-1234yf. The data in Table 11 were obtained by calculation using measured and calculated thermodynamic properties. The numbers at the top of the columns refer to FIG. 1.

TABLE 11

| Compound or variable | 540 Feed Mixture | 570 Column (510) distillate | 566 HFC-1234yf product | 585 Column (520) distillate | 586 HF product |
|---|---|---|---|---|---|
| HF, mol % | 11.4 | 30.0 | — | 20.0 | 100 |
| HFC-1234yf, mol % | 88.6 | 70.0 | 100 | 80.0 | — |
| Temp., ° C. | — | 71.2 | 80.2 | −18.4 | 36.9 |
| Pres., psi (kPa) | — | 364.7 (2515) | 366.7 (2528) | 24.7 (170) | 26.7 (184) |

What is claimed is:

1. An azeotrope or near-azeotrope composition comprising from about 64.6 mole percent to about 92.4 mole percent HFC-1234yf and hydrogen fluoride wherein said composition is characterized by a difference between dew point pressure and bubble point pressure that is less than or equal to 3%, based upon bubble point pressure.

2. The azeotrope or near-azeotrope composition of claim 1 comprising from about 64.6 mole percent to about 92.4 mole percent HFC-1234yf and from about 35.4 mole percent to about 7.6 mole percent hydrogen fluoride.

3. The azeotrope or near-azeotrope composition of claim 1 wherein said composition consists essentially of from about 64.6 mole percent to about 92.4 mole percent HFC-1234yf and from about 35.4 mole percent to about 7.6 mole percent hydrogen fluoride, wherein the vapor pressure is from about 23.2 psi (160 kPa) to about 453 psi (3123 kPa) at a temperature of from about −20° C. to about 80° C.

4. The azeotrope composition of claim 1 wherein said composition consists essentially of from about 68.9 mole percent to about 80.7 mole percent HFC-1234yf and from about 31.1 mole percent to about 19.3 mole percent hydrogen fluoride, wherein the vapor pressure is from about 23.2 psi (160 kPa) to about 453 psi (3123 kPa) at a temperature of from about −20° C. to about 80° C.

5. A process for the separation of HFC-1234yf from HFC-245cb comprising:
   a) forming a mixture of HFC-1234yf, HFC-245cb, and hydrogen fluoride; and
   b) subjecting said mixture to a distillation step from which is formed a column distillate composition comprising an azeotrope or near-azeotrope composition of hydrogen fluoride and HFC-1234yf essentially free of HFC-245cb, wherein said column distillate composition is characterized by a difference between dew point pressure and bubble point pressure that is less than or equal to 3%, based upon bubble point pressure.

6. The process of claim 5 further comprising forming a column-bottoms composition comprising HFC-245cb.

7. The process of claim 6 wherein said column-bottoms composition comprises HFC-245cb essentially free of hydrogen fluoride.

8. The process of claim 5 wherein said mixture of HFC-1234yf, HFC-245cb, and hydrogen fluoride comprises equimolar quantities of each component.

9. The process of claim 5 wherein said mixture of HFC-1234yf, HFC-245cb, and hydrogen fluoride comprises excess HFC-1234yf.

10. A process for the separation of HFC-1234yf from a mixture comprising an azeotrope or near-azeotrope composition of HFC-1234yf and hydrogen fluoride wherein said composition is characterized by a difference between dew point pressure and bubble point pressure that is less than or equal to 3%, based upon bubble point pressure, said process comprising:
   a) subjecting said mixture to a first distillation step in which a composition enriched in either (i) hydrogen fluoride or (ii) HFC-1234yf is removed as a first distillate composition with a first bottoms composition being enriched in the other of said components (i) or (ii); and
   b) subjecting said first distillate composition to a second distillation step conducted at a different pressure in which the component enriched as first bottoms composition in (a) is removed in a second distillate composition with a second bottoms composition enriched in the same component which was enriched in the first distillate composition 11. The process of claim 10 wherein said first bottoms composition or said second bottoms composition comprises HFC-1234yf essentially free of hydrogen fluoride.

12. The process of claim 10 wherein said second bottoms composition comprises hydrogen fluoride essentially free of HFC-1234yf 13. The process of claim 10 wherein said first distillation step is carried out at a pressure greater than the pressure of the second distillation step.

14. The process of claim 10 wherein said mixture consists essentially of HFC-1234yf in combination with an effective amount of hydrogen fluoride to form an azeotrope or near-azeotrope composition with hydrogen fluoride, said azeotrope or near-azeotrope composition containing from about 64.6 mole percent to about 92.4 mole percent HFC-1234yf.

15. A process for the purification of HFC-1234yf from a mixture of HFC-1234yf, HFC-245cb, and hydrogen fluoride, said process comprising:
 a) subjecting said mixture to a first distillation step to form a first distillate comprising an azeotrope or near-azeotrope composition containing HFC-1234yf and hydrogen fluoride, wherein said composition is characterized by a difference between dew point pressure and bubble point pressure that is less than or equal to 3%, based upon bubble point pressure, and a first bottoms comprising HFC-245cb;
 b) subjecting said first distillate to a second distillation step from which a composition enriched in either (i) hydrogen fluoride or (ii) HFC-1234yf is removed as a second distillate composition with a second bottoms composition being enriched in the other of said components (i) or (ii); and
 c) subjecting said second distillate composition to a third distillation step conducted at a different pressure than the second distillation step in which the component enriched in the second bottoms composition in (b) is removed as a third distillate composition with a third bottoms composition enriched in the same component that was enriched in the second distillate composition.

16. A process to produce HFC-1234yf comprising:
 a) feeding HFC-245cb to a reaction zone for dehydrofluorination to form a reaction product composition comprising HFC-1234yf, unreacted HFC-245cb and hydrogen fluoride;
 b) subjecting said reaction product composition to a first distillation step to form a first distillate composition comprising an azeotrope or near-azeotrope composition containing HFC-1234yf and hydrogen fluoride, wherein said first distillate composition is characterized by a difference between dew point pressure and bubble point pressure that is less than or equal to 3%, based upon bubble point pressure, and a first bottoms composition comprising HFC-245cb;
 c) subjecting said first distillate composition to a second distillation step from which a composition enriched in either (i) hydrogen fluoride or (ii) HFC-1234yf is removed as a second distillate composition with a second bottoms composition being enriched in the other of said components (i) or (ii); and
 d) subjecting said second distillate composition to a third distillation step conducted at a different pressure than the second distillation step in which the component enriched in the second bottoms composition in (c) is removed as a third distillate composition with a third bottoms composition enriched in the same component that was enriched in the second distillate composition.

17. The process of claim 16, further comprising recycling at least some portion of said first bottoms composition to said reaction zone.

18. The process of claim 16, further comprising recycling at least some portion of said second bottoms composition or said third bottoms composition to said reaction zone.

19. The process of claim 16, further comprising recovering at least some portion of said second bottoms composition or said third bottoms composition as HFC-1234yf essentially free of HFC-245cb and hydrogen fluoride.

20. The process of claim 16, further comprising recycling at least some portion of said second bottoms composition or said third bottoms composition to said first distillation step.

\* \* \* \* \*